United States Patent [19]

Dickey

[11] 4,228,797
[45] Oct. 21, 1980

[54] INTRAVAGINAL CONTRACEPTION METHOD

[76] Inventor: Richard P. Dickey, 5640 Read Blvd., Ste. 640, New Orleans, La. 70127

[21] Appl. No.: 945,529

[22] Filed: Sep. 25, 1978

[51] Int. Cl.³ .............................................. A61F 13/20
[52] U.S. Cl. ..................................... 128/270; 206/572
[58] Field of Search ............... 128/263, 270, 271, 285, 128/127; 206/572, 363, 553; 426/27–29, DIG. 14

[56] References Cited

U.S. PATENT DOCUMENTS

| | | | |
|---|---|---|---|
| 2,467,884 | 4/1949 | Elias | 128/270 |
| 3,262,450 | 7/1966 | Elias | 128/270 |
| 3,639,562 | 2/1972 | Gordon et al. | 128/270 |
| 4,108,180 | 8/1978 | Moehrle | 128/285 |

*Primary Examiner*—C. Fred Rosenbaum
*Attorney, Agent, or Firm*—C. Emmett Pugh & Associates

[57] ABSTRACT

A chemical contraception system is described in which the spermicidal chemical, for example, "Nonoxynol-9", is provided in a powder or tablet form and is dissolved in a solvent, primarily water, immediately before use. The solution containing the spermacide is then allowed to soak into an applicator matrix, such as a sponge or pad. The spermicide-impregnated matrix is inserted into the vagina and later removed. The system can be provided in kit form (FIGS. 1 and 2) including a storage container for the powder, a mixing container, and a measuring spoon, or in a pre-packaged form where the chemical has already been added to the sponge.

Among the preferred embodiments of the system are the use of the spermicidal chemical in powder or tablet form and the use of a sponge for vaginal retention of the spermicidal solution.

6 Claims, 4 Drawing Figures

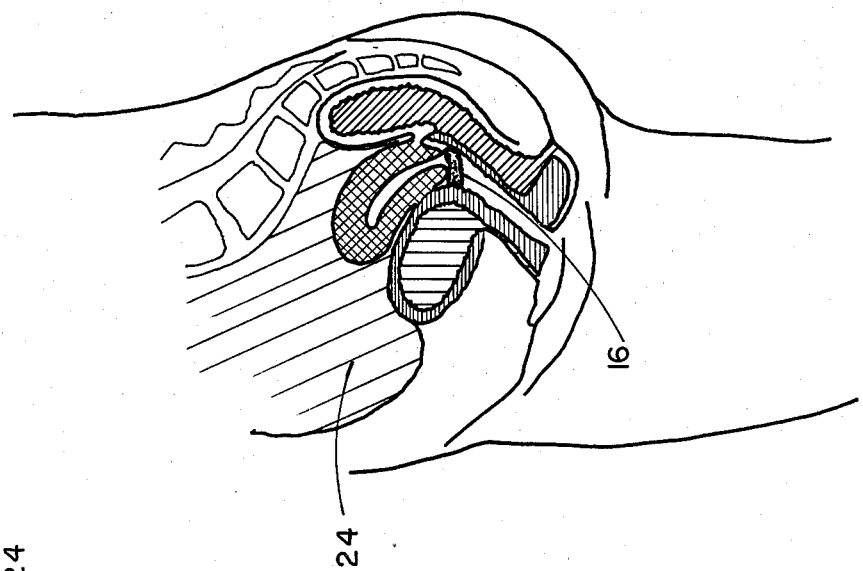
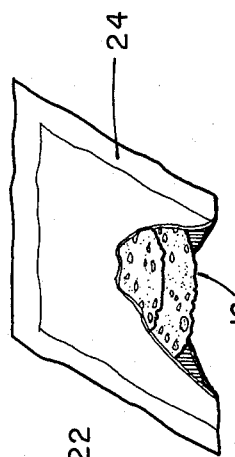
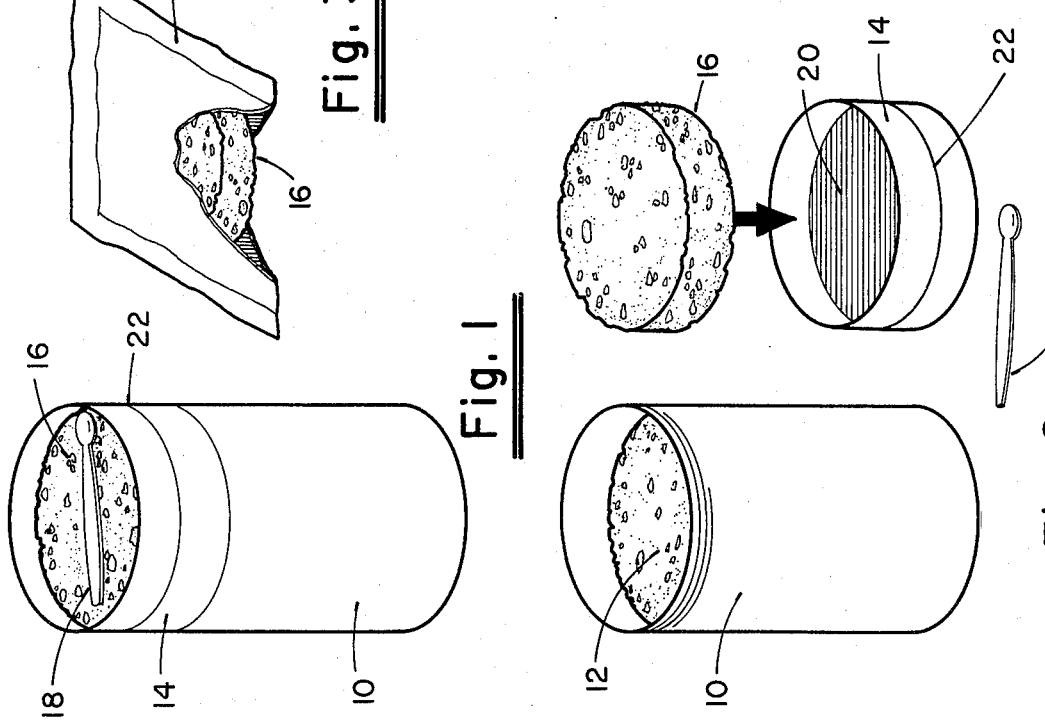

INTRAVAGINAL CONTRACEPTION METHOD

BACKGROUND OF THE INVENTION

1. Field of the Invention

The present invention relates to chemical contraception systems, and more particularly relates to an intravaginal spermicidal applicator system in which the spermatocidal agent, originally in tablet or powder form, is dissolved in an appropriate solvent immediately before use.

2. Description of the Prior Art

The use of sponges or tampons with spermicides for intravaginal contraception is known in the art. Intrauterine applicators for contraception and drug administration have been extensively developed. A variety of spermicidal foams and jellies are separately available as well.

One reason spermatocidal agents are effective is that they alter the surface tension of the spermatozoa and so immobilize them. It is believed that the greater the viscosity of the material in which the chemical is contained, the more effective it can be in altering surface tension. Theoretically, then, spermaticides are most effective when dissolved in water. The problems of using water as the solvent have been the instability of the agent when dissolved in water and the difficulty of retaining the substance within the vagina.

The present invention offers solutions to these problems. The powder or tablet form, which is dissolved immediately before using, provides the necessary stability while the use of the vaginal sponge solves the problem of vaginal retention.

Prior to the present invention, most of the preparations and methods which have been developed were beyond the means of lower income groups for whom the need for an effective contraceptive method is certainly no less important. IUD'S, steriod preparations, foams and jellies for diaphragm use are all commodities primarily available in developed wealthier countries. It is the object of this invention to provide an inexpensive, effective and convenient method of contraception which may be provided on a mass scale to underdeveloped countries at a relatively minimal cost.

Prior U.S. patents which may be of interest to the present invention of which applicant is aware are listed below:

| | | |
|---|---|---|
| 3,865,300 | 3,903,880 | 3,948,262 |
| 3,892,842 | 3,905,360 | 3,971,367 |
| 3,895,103 | 3,921,636 | 3,993,072 |
| 3,896,819 | 3,948,254 | 3,995,634 |
| 4,014,987 | 3,920,805 | 3,993,073 |

Prior publications which may be of interest to the present invention of which applicant is aware are listed below:

BENNETT, JOHN P., CHEMICAL CONTRACEPTION, Columbia University Press, (1974).

GEORGE WASHINGTON UNIVERSITY, "Population Reports", Series H, No. 3 (January 1975).

GENERAL DISCUSSION OF THE INVENTION

Accordingly, the present invention provides a spermicidal chemical such as "Nonoxynol 9", preferably buffered to the vaginal pH, 4.5, in powder or tablet form for later adding to an applicator immediately prior to use or pre-added to the applicator prior to packaging.

The following is an exemplary list of chemicals which may be used in the present invention:

TABLE I

| | |
|---|---|
| Chloramine | Cuprein lactate |
| Phenal mercuric borate | Sodiaum dichlorsulfamide benzoate |
| Phenyl mercuric acetate | Cetylpridinium bromide |
| Phenyl mercuric nitrate | Dioctyl sodium sulfosucciaate |
| Benzalkonium chloride | Zince phenosulfonate |
| p. Sulfondichloraminobenzoic acid | Alkylphenoxpolyethoxyethanol |
| Dimethylaminoacetic acid | Hexylresorcinol |
| Quine hydrochloride | Resorcicinol |
| Nonylphenoxpolyethoxyethanol | Sodium lauryl sulfate |
| Benzethonium chloride | Dodecylamidochlorobenzylate |
| p-Tri-isopropylephoxypoly ethoxethanol | Dodecaethylene glycol monolaurate |
| Aluminum perlactate | |

The above list is not intended to be exclusive but rather to show the broad applicability of the method. Any water soluble spermicide may be used. The chemical is dissolved in a suitable solvent, preferably water, and the resolvement solution is allowed to soak into an appropriate matrix, such as a sponge or pad. The sponge may then be placed in the vagina prior to coitus and removed afterwards.

A variety of alternatives are possible within the present invention. The chemical powder, or tablets, may be provided in bulk form, allowing the user to measure out the appropriate quantity for each use, dissolve it, and place the sponge in the solution for absorbtion. Cost factors may be made quite low on this basis.

Alternatively, the powder or tablets may be dispensed in single application quantities for greater convenience. Or, a sponge and a premeasured quantity of chemical in powder, table or solution may be packaged together as a kit.

BRIEF DESCRIPTION OF THE DRAWINGS

For a further understanding of the nature and objects of the present invention, reference should be had to the following detailed description, taken in conjunction with the accompanying drawings, in which like parts are given like reference numerals and wherein:

FIG. 1 is an isometric view of a multiple application kit for use with the method of the present invention.

FIG. 2 is an isometric view of the disassembled kit shown in FIG. 1 showing its method of use; while FIG. 3 is a partial cutaway, isometric view of a single application packet for alternative use with the method of the present invention; and FIG. 4 is a cross-sectional view of a female torso showing the applicator of the present invention in the proper position for effective contraception.

DETAILED DESCRIPTION OF THE PREFERRED EMBODIMENTS

In the preferred embodiment of the present invention a quantity of a spermicidal chemical, such as "Nonoxynol 9," is provided a user along with a measuring spoon and a small reusable sponge or pad suitable for insertion into the vagina as a spermicidal applicator. FIG. 1 shows the preferred embodiment in kit form. Although "Nonoxynol 9" has been referred to, it is to be understood that any water soluble spermicide may be used, for example, any of the named chemicals listed in Table 1, for example dodecaethylene glycol monolaurate, and methoxpolyoxethelene glycol 555 laurate, just to name a few.

Referring now more particularly to the drawings, FIG. 1 shows an assembled kit providing the necessary elements for the application method of the present invention, while FIG. 2 shows the same kit disassembled and prepared for use.

A canister or box 10 containing a sufficient quantity of spermicidal chemical 12 in powder form for a large number of applications is provided with a cap assembly 14 having an upper cavity containing a sponge 16 and measuring spoon 18. The chemical 12 is buffered with boric acid to a pH of 4.5 to assure maintenance of a healthy vagina biology. A further top or sealing cap (not illustrated for simplicity purposes) is included to close off the top of cap 14.

The cap 14 is removed and placed on a flat surface with the cavity facing up. Cavity 20 forms a bottom-sealed, water-tight cup for measuring and applicator use. The sponge 16 and spoon 18 are removed, a small amount of chemical is measured out with spoon 18 and placed in the cavity. Water is added to an appropriately placed indicator line 15 and stirred to insure complete dissolution of the chemical. The sponge 16 is then placed in the solution 20, as indicated in FIG. 2, and squeezed a few times to cause it to soak up the solution 20.

The solution-soaked sponge is then folded and inserted into the vagina against the cervix, much as a diaphragm is inserted. FIG. 4 shows the sponge 16 in proper placement.

The sponge can be approximately four to eight cm. in diameter and two to four cm. thick. It may be made of conventional sponge materials that provide a soft and pliable material when wet. The primary function of the sponge is to deliver the spermicidal chemical to the vagina and allow it to remain there for a period of four to six hours and provide effective contraceptive action at the users convenience. A secondary function of the sponge is to entrap the spermatozoa and prevent their migration to the uterus.

While full saturation of the sponge is desired for maximum contraceptive protection, effective protection may be afforded with as little as half-saturation of the sponge.

Recommended matrix size depends primarily upon the woman's parous history. The following table provides preferred dimensions for the three parous types of women:

TABLE II

| Type of Woman | Dimensions (Diameter & Thickness) | Capacity |
| --- | --- | --- |
| Nulliparous | 4.5 cm × 2.7 cm | 30 ml |
| Primiparous | 5.4 cm × 2.7 cm | 45 ml |
| Multiparous | 6.2 cm × 2.7 cm | 60 ml |

The amount of active ingredient, for example, "Nonoxynol 9", required to provide contraceptive potency comparable to or exceeding present vaginal spermacidal foams, creams and gels for each of the above matricees is as follows:

TABLE III

| Spermicidal Compound | Volume Meter | Concentration |
| --- | --- | --- |
| 3.6 mg | 30 ml | 0.12 mg/ml |
| 5.4 mg | 45 ml | 0.12 mg/ml |

TABLE III-continued

| Spermicidal Compound | Volume Meter | Concentration |
| --- | --- | --- |
| 7.2 mg | 60 ml | 0.12 mg/ml |

By way of comparison, "Delfen Foam" provides five ml of a 0.12 mg/ml solution in a single application.

The concentration of 0.12 mg/ml "Nonoxynol 9" has been shown to be capable of immobilizing 100% of human sperm in less than twenty seconds, at a concentration of 0.12 ml semen per eleven ml fluid. Homm, R. E., Doscher, E. G., Hummel, E. G., and Greenslade, F. C., "Contraception" 13:479, (1976).

The preferred embodiment calls for providing the chemical in powder form. However, it may alternatively be provided in tablet form. In either case, bulk supplies may be inexpensively produced and shipped for economically feasible birth control programs, either in the United States or abroad.

FIG. 3 shows an alternative embodiment for use in the present invention. A sponge 16' may be provided, pre-saturated with spermicidal solution in a sealed package 24 made, for example, of aluminum foil. Or, the sponge 16' may be provided in such a package with the chemical permeated throughout. The sponge 16' would then be activated by soaking in the appropriate amount of water.

This completes the description of the embodiments illustrated herein. However, the invention is not limited to the particular details of construction, elements and processes described as many equivalents will suggest themselves to those schooled in the art. It is accordingly desired that the appended claims be given a broad interpretation commensurate with the scope of the invention within the art.

What is claimed is:

1. A method of intravaginal contraception comprising the following steps:
   (a) providing to the user in powdered or tablet, packaged form a spermicidal chemical to be kept by the user in its packaged form until needed;
   (b) removing the spermicidal from its packaging just prior to use and dissolving it in water;
   (c) just prior to use impregnating a suitable shaped matrix of either organic or inorganic material with the resolvent solution;
   (d) placing the solution impregnated matrix into the vagina prior to coitus; and
   (e) removing the matrix following coitus.

2. A method of intravaginal contraception according to claim 1 further comprising the step of rinsing the matrix following removal to permit re-use of the matrix.

3. A method of intravaginal contraception according to claim 1 further comprising the steps of:
   (a) placing the solution impregnated matrix in a solvent of water-tight sealed package to store the matrix for later use; and
   (b) removing the solution impregnated matrix from the sealed package for placement into the vagina.

4. A method of intravaginal contraception according to claim 1 wherein there is further included in step "a" the further steps of:
   providing a container for holding a multiple-application quantity of said spermicidal chemical and a cap for closing said container having a water-tight cavity for holding said matrix which is of a size to fit in said cavity for storage between uses and of a suitable size for receiving the ingredients of a single application quantity of said spermicidal solution; and adding water and an appropriate amount of said spermicidal chemical for an application into said cavity and mixing them together; and in step "c" the step of placing said matrix in said cavity with said spermicidal chemical and water solution to impregnate it.

5. A method of intravaginal contraception according to claim 4 wherein in step "a-i" there is included the steps of packaging a measuring spoon with said container and using said measuring spoon to remove the appropriate amount of spermicidal chemical into said cavity and to mix said spermicidal chemical and water together.

6. A method of intravaginal contraception according to claim 4 wherein said cavity includes a graduation marking to facilitate measuring the water to be added to said cavity; and wherein in step "a-i" there is included the step of using said graduation marking as a guide in adding water to said cavity.

* * * * *